United States Patent [19]
Groten et al.

[11] Patent Number: 5,316,832
[45] Date of Patent: May 31, 1994

[54] BIODEGRADABLE SHEET FOR CULTURING SEWAGE DENITRIFIERS

[75] Inventors: Robert Groten, Weinheim/Steinklingen; Gerhard Heidecke, Bensheim; Thomas Mannsbart, Edingen-Neckarhausen; Volker Siekermann, Fürth, all of Fed. Rep. of Germany

[73] Assignee: Carl Freudenberg, Weinheim/Bergstrasse, Fed. Rep. of Germany

[21] Appl. No.: 57,585

[22] Filed: May 4, 1993

[30] Foreign Application Priority Data

Jun. 25, 1992 [DE] Fed. Rep. of Germany ....... 4220795

[51] Int. Cl.$^5$ ............................................. D03D 3/00
[52] U.S. Cl. .................... 428/224; 210/903; 428/296
[58] Field of Search ................ 210/903; 428/224, 296

[56] References Cited

U.S. PATENT DOCUMENTS 4,362,777 12/1982 Miller ................................. 428/296
4,769,279 9/1988 Graham ............................. 428/296

Primary Examiner—James J. Bell
Attorney, Agent, or Firm—Sprung Horn Kramer & Woods

[57] ABSTRACT

A biodegradable substrate in sheet form which acts as a source of carbon and hydrogen in oxygen-poor water in biological water-treatment stages. The substrate is covered with at least one layer of a population of spontaneously growing denitrifiers. The substrate is a spun-bonded non-woven fabric weighing 10 to 1500 g/m$^2$. It has a prescribed effective area that results in an ideal rate of denitrification per clarification stage at a prescribed rate of flow per area and time. The fabric is comprised of at least 50% continuous poly-$\epsilon$-caprolactone filament with a mean molecular weight of 20,000 to 70,000. The individual filaments adhere to each other at their intersections.

5 Claims, No Drawings

BIODEGRADABLE SHEET FOR CULTURING SEWAGE DENITRIFIERS

BACKGROUND OF THE INVENTION

The present invention concerns a biodegradable sheet for culturing sewage denitrifiers that multiply spontaneously. Denitrifiers are bacteria and other microbes that decompose nitrates.

A biodegradable culture medium (polyhydroxybutyrate plus polyhydroxyvalerate) derived from poly-β-hydroxybutyric acid and poly-β-hydroxyvaleric acid and intended for biological nitrate elimination (denitrification) is described by Wolf-Rüdiger Müller in the article "Abwasser mit zerkleinertem Kunststoff reinigen" in Umwelt, Vol. 20 (1990). Sheets of the material are obtained biotechnologically in fermenters by bacterial metabolism. Colonization with populations of denitrifiers and the potential for denitrification without introducing other, foreign, organic hydrogen-and-carbon donors has been studied. The nitrogen-oxide level subsequent to denitrification has never been investigated.

Since the microbes can obtain hydrogen and carbon from the sheet, there is no need of the toxic methyl alcohol as a donor. This feature is particularly desirable from the aspect of rendering the water potable. The material also makes it possible to carry out denitrification in a column or basin subsequent to filtration and nitrification as a stage in the treatment of sewage and underground water. The process involves intermediate accommodation of the used substrate in a column to allow fresh denitrifier populations to grow.

One drawback of this system is the expense incurred in biosynthesizing the substrate, which prevents its extensive use. Another is that not very much polyhydroxybutyrate plus polyhydroxyvalerate (PHB-PHV) can be biotechnologically produced in fermenters per year. Again, the systems can be processed only into sheets with a limited and unexpandable surface and hence a limited capacity for absorbing denitrifiers.

SUMMARY OF THE INVENTION

The principal object of the present invention is to provide an inexpensive sheet for culturing denitrifiers that can be produced in large quantities, that will be easy to handle, and that will be even more effective as the sole donor of hydrogen and carbon. It will be possible to employ this sheet uncontaminated in nitrate-charged drinking-water treatment facilities and to denitrify ($NO_x \rightarrow N_2$) at a rate of at least 45% (downstream of a nitrification stage). There will be a higher ratio of cultivable surface to weight than in a conventional plastic sheet. This object, as well as other objects which will become apparent from the discussion that follows, are achieved, in accordance with the present invention, by providing as a substrate a sheet of non-woven fabric weighing 10 to 1500 g/m$^2$. Such a non-woven fabric is totally biodegradable. It is a copolymer of at least 50% by weight of spun poly-ε-caprolactone filaments. The second component can be a biodegradable polyhydroxybutyrate, a copolymer of polyhydroxybutyrate and hydroxyvalerate, a polylactide, or a polyesterurethane.

This non-woven fabric weighs 10 to 100 g/m$^2$. Its filaments hot bond together without any adhesive at their intersections, determining the inherent strength. The filaments should be as slender as possible to keep the denitrifier-cultivatable surface as extensive as possible. Basically, however, industrially produced filaments of any diameter can be employed in the present invention.

Flavobacteria, Agrobacteria, and pseudomonas, for example, are appropriate as denitrifiers.

How much of the sheet is needed for each stage of treatment must be determined empirically. The objective is ideal performance in terms of the prevailing rate of sewage flowing through the sheet per area per unit of time.

If the sewage contains 15 to 25 mg of $NO_x$-N/l, which is the same as 65 to 110 mg of $NO_x$/l, and if analysis demonstrates a monthly denitrification-surface consumption of 0.008 m$^2$ and a monthly water through-flow of 0.25 m$^3$, the quotient of surface to throughflow will reduce to 0.032 m$^2$ of sheet per m$^3$ of water for ideal treatment.

Levels this high are valid only for the aforesaid $NO_x$-—concentration range. Lower levels can be expected for drinking-water treatment because fewer denitrifiers are employed.

Poly-ε-caprolactone is known to be easy to spin from a melt into filaments of any length and to biodegrade in the environment when exposed to organisms in the soil. The filaments have a molecular weight of 20,000 to 70,000.

The non-woven fabric is manufactured in accordance with known technologies by melting the poly-ε-caprolactone or biodegradable mixture at 150° to 220° C. and pumping it through spinnerets to obtain the filament. The filament is drawn through tempered air, cooled, and spun bonded into a sheet. No further compacting is necessary. The temperature of the melt and of the drawing air can be optimized to ensure that the polymer will not have completely crystallized while the new filaments are being spun bonded. This, together with the still high enough filament-surface temperature, will ensure enough tackiness for automatic hot bonding at the filament intersections.

The range of molecular weights is limited at the low end by the batch being too waxy to spin and by the poly-ε-caprolactone being too brittle at the high end.

The non-woven fabric in accordance with the invention can consist entirely of, and must consist of at least 50% of, poly-ε-caprolactone by weight. The second component can be one of the aforesaid biodegradable polyesters. The combinations are easier to spin, and bond automatically into a fabric that will completely biodegrade.

Although the second components themselves are also biodegradable, they are difficult or impossible to spin. Only when blended with poly-ε-caprolactone are they appropriate for conventional spinning. The non-woven fabric substrates in accordance with the invention will stretch at least 50% and are permanently hydrophilic.

The biologically active microorganisms are introduced by spontaneous growth. Native denitrifier populations will surprisingly participate in the colonies even anaerobically. All that is necessary is to leave the fabric in a denitrification column or basin and let the water that is to be denitrified flow through it.

To accelerate growth, however, it is practical to bring an already colonized substrate into contact with a new and as yet uncolonized fabric just before it is used.

A completely colonized substrate will have several layers of denitrifier. The fabric is stretched on frames that are heavy enough to hold it under the water. A series of several frames is practical. They can also be made of poly-ε-caprolactone.

Since the substrates in accordance with the invention are non-toxic, they can also be used in drinking-water processing plants. They denitrify ($NO_x \rightarrow N_2$) at least twice as fast in relation to surface as sheets of PHB-PHV. Water without too much nitrate is denitrified almost 100%. All of this is due to the high density of the population at the surface of the fabric.

EXAMPLE 1

Manufacturing a non-woven poly-ε-caprolactone fabric: Poly-ε-caprolactone melting at 60° C. and with a melt-flow index of 10 g/10 min at 130° C./2.16 kg is melted in an extruder at 185° C. The temperature of spinning is 203° C. The material is spun out of spinnerets and drawn in air at 50° C.

The continuous drawn filaments are intercepted on a traveling screen, bonding together at their intersections without further compaction. The finished fabric weighs 22 g/m².

The web was prepared for testing by wrapping it into six loops, a number previously demonstrated to be ideal for denitrification, and fusing the filaments at the edges to create a frame. The resulting structure was then introduced into a downstream denitrification basin of the same width in a drinking-water and sewage treatment plant.

Colonizing the fabric: The immersed fabric served as a natural attractant for denitrifying microorganisms from the ground water or sewage. Preliminary testing indicated that the sessile species most capable of metabolizing the proffered biodegradable non-woven substrate or its fission products were of the Pseudomonas and Bacillus genera.

Growth was affected by temperature (30° C.), pH (8.0), oxygen level subsequent to nitrification (0.5 mg $O_2$/l), and length of residence of the water being treated (3 hours).

How the substrate was employed in a treatment plant will now be specified.

1. Pilot-Plant Column Packed With Non-Woven

Sewage from an industrial water-treatment plant was precipitated and flocculated. The pilot-plant volumes and volumetric flow rates were 1/1 000 000 of the industrial scale.

Any chemical sludge was removed by sedimentation before the sewage was advanced to the nitrification stage.

The biological sludge was sedimented out in a sedimentation basin subsequent to, and returned to, the nitrification stage. The clear stage flowed up through the denitrification stage from below. The column was Plexiglas packed with a stationary bed of granulated poly-ε-caprolactone.

The bed was inoculated at the commencement of the test with denitrifiers from an adjacent laboratory-scale apparatus.

a) Version with downstream nitrification: The efficiency of the denitrification stage was determined with the aforesaid pilot plant and compared with results from a similar plant with denitrification upstream. The rates became comparable in less than 3 weeks of adaptation.

b) Version with downstream denitrification and a low concentration of $NO_x$: This test was intended to determine whether the nitrification rate could be decreased by inhibiting the denitrifier population's efficiency. No effect was observed. The nitrates and nitrites were almost completely eliminated.

2. A Column Packed With Non-Woven In Real Sewage Conditions (With Sensitive Nitrification)

The design was essentially reproduced with an open basin matching the geometry of the sewage-treatment basin. Six loops of an unmounted web of material was introduced into the denitrification basin. The sewage was introduced at the upper edge of the front wall and extracted at the bottom of the opposite wall.

Weekly titration and ion chromatography revealed the nitrogen balance sheet ($NH_4^+$, KI-M, and $NO_x$) at the intake and outlet of the denitrification stage and hence the rate of $NO_x$ to $N_2$.

| Test 1, | Version a): | 40% |
|---|---|---|
|  | Version b): | >80% |
| Test 2: |  | >70% |

The results for the same quantity of single layers of 100-μm thick sheets of PHB-PHV under real conditions were less than 10%.

EXAMPLE 2

Manufacturing a spun-bonded fabric of poly-ε-caprolactone and polyhydroxybutyrate plus polyhydroxyvalerate: A blend of 80% poly-ε-caprolactone and 20% polyhydroxybutyrate-polyhydroxyvalerate copolymer by weight with a melt-flow index of 34 g/10 min at 190° C./2.16 kg is melted at 182° C. The filaments emerging from the spinnerets are drawn in air at 40° C. The continuous filaments are intercepted on a conveyor belt. The fibers bond together without external pressure. The resulting non-woven weighs 23 g/m². It is colonized and tested as described with reference to Example 1.

The results were:

| Test 1, | Version a): | 35% |
|---|---|---|
|  | Version b): | >75% |
| Test 2: |  | >65% |

There has thus been shown and described a novel biodegradable sheet for culturing sewage denitrifiers which fulfills all the objects and advantages sought therefor. Many changes, modifications, variations and other uses and applications of the subject invention will, however, become apparent to those skilled in the art after considering this specification which discloses the preferred embodiments thereof. All such changes, modifications, variations and other uses and applications which do not depart from the spirit and scope of the invention are deemed to be covered by the invention, which is to be limited only by the claims which follow.

What is claimed is:

1. A biodegradable substrate in sheet form for providing a source of carbon and hydrogen in oxygen-poor water in biological water-treatment stages when covered with at least one layer of a population of spontaneously growing denitrifiers, said substrate comprising a spun-bonded non-woven fabric weighing 10 to 1500 g/m², said fabric including at least 50% continuous poly-ε-caprolactone filaments with a mean molecular weight of 20,000 to 70,000, whereby the individual filaments adhere to each other at their intersections.

2. The substrate defined in claim 1, wherein the filaments are made of 100% poly-ε-caprolactone.

3. The substrate defined in claim 1, wherein the filaments are made of a two-component polymer blend, one component of which is poly-ε-caprolactone and the other a biodegradable copolymer of polyhydroxybutyrate and polyhydroxyvalerate, a polylactide, or a polyesterurethane.

4. The substrate defined in claim 1, covered with at least one layer of a population of spontaneously growing denitrifiers.

5. In the denitrification of a nitrate-containing water wherein the water is contacted with a denitrifier, the improvement wherein the denitrifier comprises a sheet according to claim 1.

* * * * *